(12) United States Patent
Halder Joshi et al.

(10) Patent No.: US 12,144,878 B2
(45) Date of Patent: Nov. 19, 2024

(54) MULTIPLE-COMPARTMENT DEVICE COMPRISING AT LEAST ONE INTERNAL FRANGIBLE SEAL CONTAINING A KERATIN FIBERS DYEING COMPOSITION

(71) Applicant: L'ORÉAL, Paris (FR)

(72) Inventors: Shilpa Halder Joshi, Mumbai (IN); Amer Alkahwaji, Clark, NJ (US); Anand Mahadeshwar, Mumbai (IN); Soumyadip Paul, Mumbai (IN); Chandra Bhan, Mumbai (IN)

(73) Assignee: L'OREAL, Paris (FR)

( * ) Notice: Subject to any disclaimer, the term of this patent is extended or adjusted under 35 U.S.C. 154(b) by 123 days.

(21) Appl. No.: 17/787,180

(22) PCT Filed: Dec. 10, 2020

(86) PCT No.: PCT/IN2020/051015
§ 371 (c)(1),
(2) Date: Jun. 17, 2022

(87) PCT Pub. No.: WO2021/124348
PCT Pub. Date: Jun. 24, 2021

(65) Prior Publication Data
US 2023/0049617 A1 Feb. 16, 2023

(30) Foreign Application Priority Data
Dec. 20, 2019 (IN) .............................. 201921053251

(51) Int. Cl.
*A61Q 5/10* (2006.01)
*A61K 8/22* (2006.01)
*A61K 8/41* (2006.01)

(52) U.S. Cl.
CPC ................ *A61K 8/22* (2013.01); *A61K 8/416* (2013.01); *A61Q 5/10* (2013.01); *A61K 2800/4322* (2013.01); *A61K 2800/882* (2013.01)

(58) Field of Classification Search
CPC .. A61K 8/22; A61K 8/416; A61K 2800/4322; A61K 2800/882; A61K 8/347;
(Continued)

(56) References Cited

U.S. PATENT DOCUMENTS 3,580,340 A 5/1971 Brown
3,635,261 A * 1/1972 Morane ................. B65D 83/42
141/3
(Continued)

FOREIGN PATENT DOCUMENTS

CN 107921293 A * 4/2018 ............... A61Q 5/10
DE 2359399 A1 6/1975
(Continued)

OTHER PUBLICATIONS

International Search Report and Written Opinion for PCT/IN2020/051015, dated Mar. 29, 2021.

*Primary Examiner* — Eisa B Elhilo
(74) *Attorney, Agent, or Firm* — THE MARBURY LAW GROUP, PLLC

(57) ABSTRACT

The present invention relates to a multiple-compartment device (1) composed of a closed envelop (2) divided in at least two distinct compartments (7a) and (7b) separated from one another by at least one internal frangible seal (8), wherein one of the compartments (7a) containing a composition (A), comprising one oxidation dye precursor, one anionic surfactant, one amphoteric surfactant chosen from betaine; and another one of the compartments (7b) containing an oxidizing composition (B) comprising at least one oxidizing agent.

19 Claims, 2 Drawing Sheets

Figure 1:
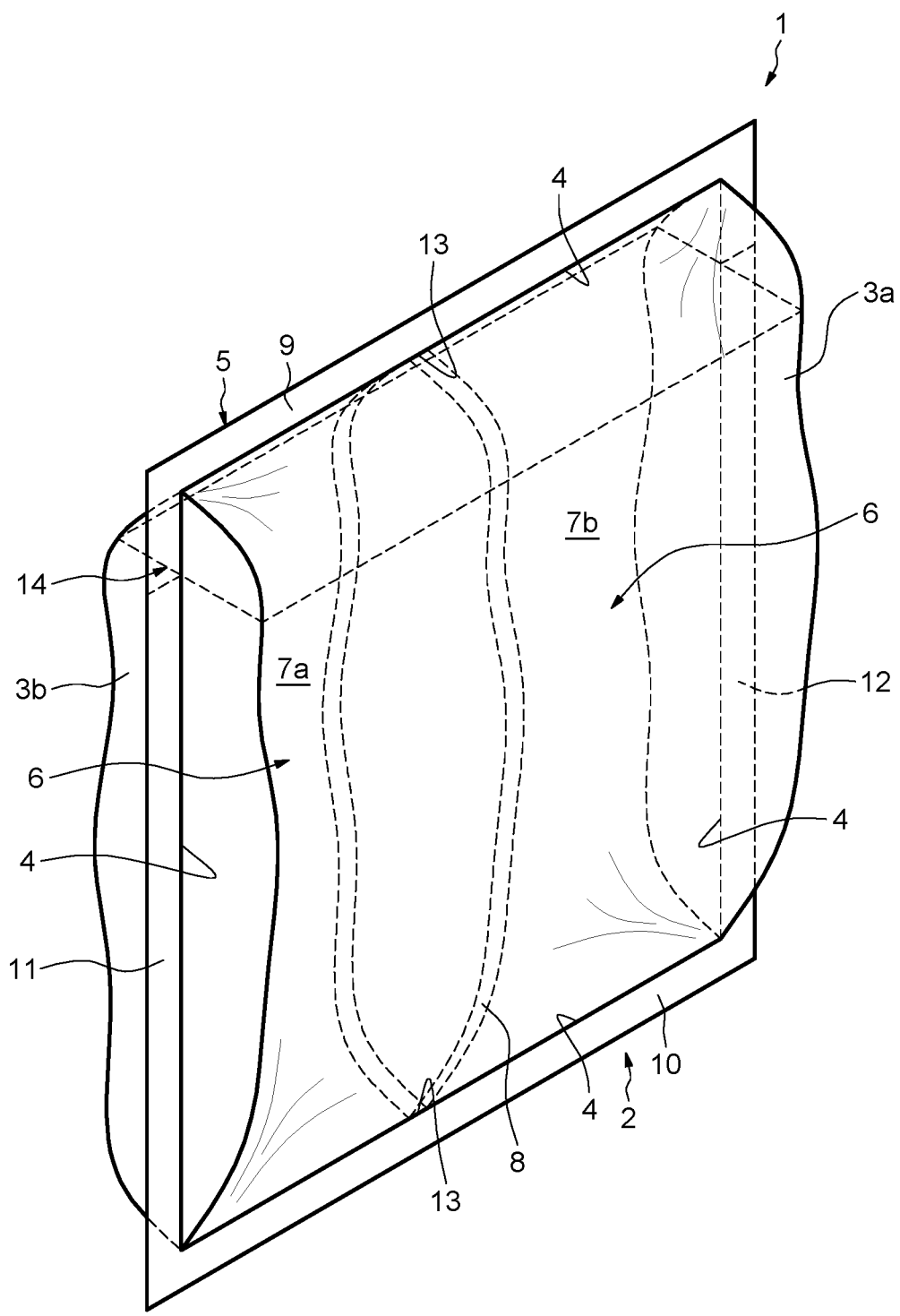

(58) Field of Classification Search
CPC ...... A61K 8/411; A61K 8/415; A61K 8/8152; A61K 2800/88; A61K 8/0204; A61K 8/44; A61K 8/463; A61K 8/8147; A61Q 5/10
USPC .......................................................... 8/405
See application file for complete search history.

(56) References Cited

U.S. PATENT DOCUMENTS

| | | | |
|---|---|---|---|
| 3,915,921 | A | 10/1975 | Schlatzer, Jr. |
| 4,003,699 | A | 1/1977 | Rose et al. |
| RE30,199 | E | 1/1980 | Rose et al. |
| 4,509,949 | A | 4/1985 | Huang et al. |
| 5,061,289 | A | 10/1991 | Clausen et al. |
| 5,534,267 | A | 7/1996 | Neunhoeffer et al. |
| 5,663,366 | A | 9/1997 | Neunhoeffer et al. |
| 5,766,576 | A | 6/1998 | Löwe et al. |
| 6,099,592 | A | 8/2000 | Vidal et al. |
| 6,284,003 | B1 | 9/2001 | Rose et al. |
| 6,730,789 | B1 | 5/2004 | Birault et al. |
| 10,307,354 | B2 | 6/2019 | Gebert-Schwarzwaelder et al. |
| 2008/0163883 | A1* | 7/2008 | Cottard .................... A61Q 5/10 8/409 |

FOREIGN PATENT DOCUMENTS

| | | |
|---|---|---|
| DE | 3843892 A1 | 6/1990 |
| DE | 4133957 A1 | 4/1993 |
| DE | 19543988 A1 | 5/1997 |
| EP | 0173109 A2 | 3/1986 |
| EP | 0216479 A1 | 4/1987 |
| EP | 0770375 A1 | 5/1997 |
| EP | 1631508 A2 | 3/2006 |
| FR | 2733749 A1 | 11/1996 |
| FR | 2801308 A1 | 5/2001 |
| FR | 2886136 A1 | 12/2006 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 96/15765 A1 | 5/1996 |
| WO | 2004/108404 A2 | 12/2004 |
| WO | 2006/027279 A2 | 3/2006 |
| WO | 2013/060862 A1 | 5/2013 |
| WO | 2013/144243 A2 | 10/2013 |
| WO | 2014/020146 A2 | 2/2014 |
| WO | 2014/100971 A1 | 7/2014 |
| WO | 2016/115674 A1 | 7/2016 |
| WO | WO 2017021511 A1 * 2/2017 ................ A61Q 5/10 |
| WO | 2019/121503 A2 | 6/2019 |
| WO | WO 2019121504 A2 * 6/2019 ................ A61Q 5/65 |

* cited by examiner

MULTIPLE-COMPARTMENT DEVICE COMPRISING AT LEAST ONE INTERNAL FRANGIBLE SEAL CONTAINING A KERATIN FIBERS DYEING COMPOSITION

CROSS REFERENCE TO RELATED APPLICATION

This is a national stage application of PCT/IN2020/051015, filed internationally on Dec. 10, 2020, which claims priority to India Application No. 201921053251, filed on Dec. 20, 2019, the contents of both of which are incorporated by reference herein in their entireties.

FIELD OF THE INVENTION

The present invention relates to a dyeing keratin fibers composition, more specifically, it refers to a multiple-compartment device composed of a closed envelop divided in at least two distinct compartments separated from one another by at least one internal frangible seal, wherein at least one of the compartments contains a composition (A) comprising oxidation dye precursors, anionic surfactants and amphoteric surfactants chosen from betaine. The present invention relates also to a method for dyeing keratin fibres, and in particular human keratin fibres, using the multiple-compartment device.

BACKGROUND OF THE INVENTION

It is known practice to dye keratin fibres, and in particular human hair, with dye compositions containing oxidation dye precursors, which are generally known as "oxidation bases", in particular ortho- or para-phenylenediamines, ortho- or para-aminophenols and heterocyclic bases.

Oxidation dye precursors are compounds that are initially uncoloured or sparingly coloured, which develop their dyeing power on the hair in the presence of oxidizing agents, leading to the formation of coloured compounds. The formation of these coloured compounds results either from an oxidative condensation of the "oxidation bases" with themselves, or from an oxidative condensation of the "oxidation bases" with coloration-modifying compounds, or "couplers", which are generally present in the dye compositions used in oxidation dyeing and are represented more particularly by meta-phenylenediamines, meta-aminophenols, meta-diphenols and certain heterocyclic compounds.

The variety of molecules used, consisting on the one hand of the "oxidation bases" and on the other hand of the "couplers", allows a very rich palette of colours to be obtained.

To facilitate the application of dye compositions, it is already known to use two-compartment devices composed of a closed envelop divided in at least two distinct compartments separated from another by at least one internal frangible seal as disclosed for example in WO2014/100971. One compartment contains a composition comprising oxidation dye precursor and one other compartment contains an oxidation composition comprising an oxidation agent. Such devices facilitate the mixing of the compositions and allow an easy application on the head, while providing good dyeing properties in short time.

There is a need to further improve the dyeing properties obtained by such two-compartment devices while maintaining an easy application and a short treatment time.

SUMMARY OF THE INVENTION

The aim of the present invention is achieved by a multiple-compartment device composed of a closed envelop, made of at least two flexible sidewalls secured together along their peripheral edges, defining a sealed perimeter and an internal volume; said internal volume being divided in at least two distinct compartments, separated from one another by at least one internal frangible seal, wherein at least one of the compartments contains a composition (A) comprising at least one oxidation dye precursor; at least one anionic surfactant and at least one amphoteric surfactant chosen from betaine, and, another one of the compartments containing an oxidizing composition (B) comprising at least one oxidizing agent, compositions (A) and (B) being intended to be mixed to obtain a dyeing composition for dyeing keratin fibers.

Another object of the present invention concerns a method for dyeing keratin fibres, wherein the following steps are successively performed:
- applying a sustained pressure to the closed envelop in a region of at least one compartment of a multiple-compartment device as defined previously, in order to break the internal frangible seal,
- opening the closed envelop of said multiple-compartment device, and
- applying the mixture of compositions (A) and (B), as defined previously, on said keratin fibres.

Preferably, the keratin fibers according to the present invention are human keratin fibers, preferably the hair.

The multiple-compartment device according to the present invention is convenient, easy to handle and time-saving.

Indeed, the frangible seal is easily broken by pressing one of the compartments. The oxidizing dye precursors are then instantly mixed with the oxidizing composition within the closed envelop, the dyeing composition can then directly be applied on the keratin fibres. Spreading of the mixture all over the head is easy.

The present invention provides also better dyeing properties, especially powerful, intensive and/or chromatic coloration and the composition is easy to rinse.

Figure 2:
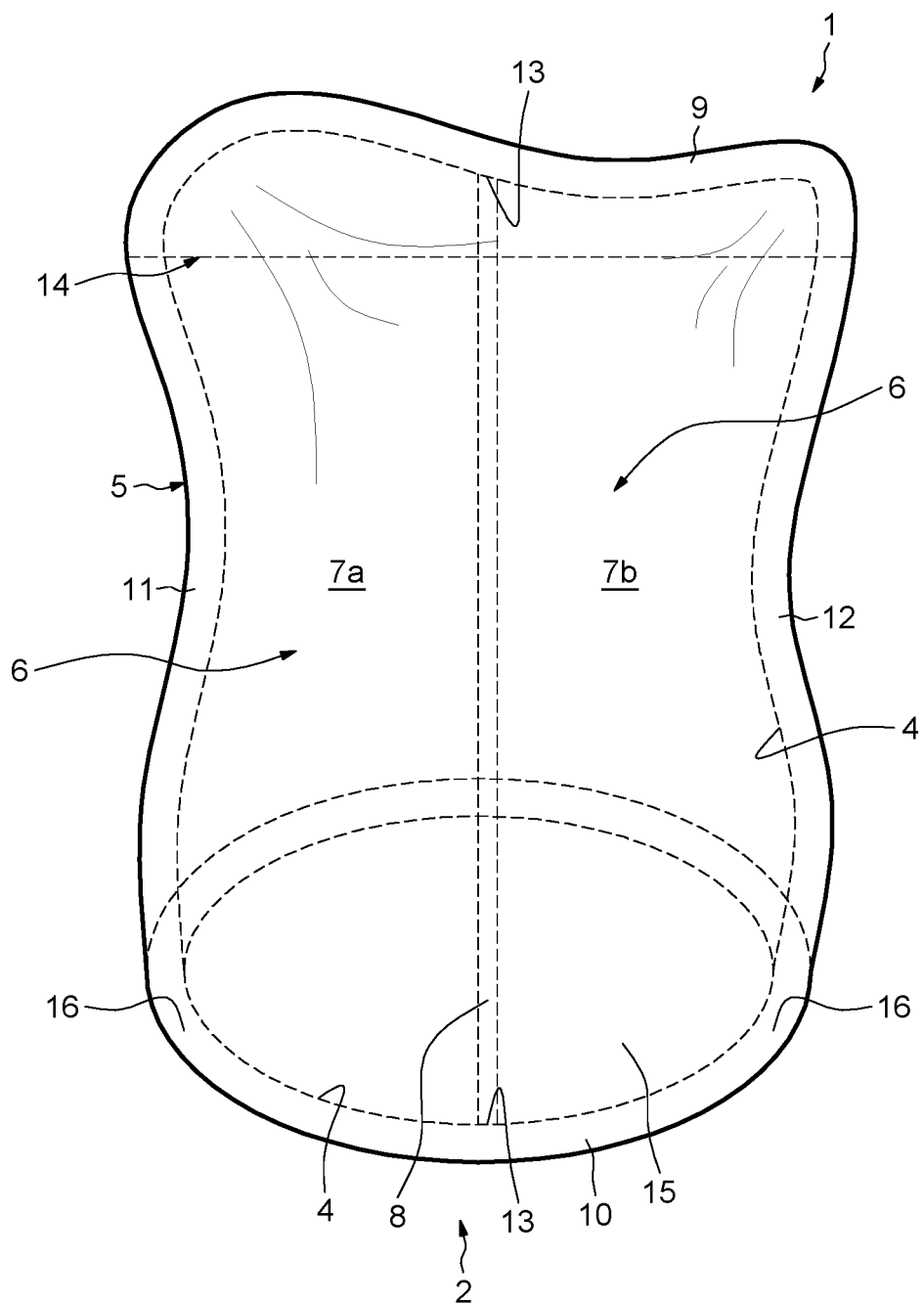

Other subjects, characteristics, aspects and advantages of the invention will emerge even more clearly on reading the description and the examples that follow, with reference to the drawings, in which:

FIG. 1 schematically shows an example of multiple-compartment device according to the invention; and FIG. 2 shows a variant embodiment of the multiple-compartment device from FIG. 1.

DETAILED DESCRIPTION OF THE INVENTION

In the description, the terms "at least a" or "at least one" are equivalent to "one or more".

The term "flexible" is used to describe a material, which deforms, but does not break, under the pressure exerted by a user. This term is not synonymous with the term "elastic".

In other words, the term "flexible" is used to describe an element which bends without stretching and without plastic deformation under the action of a force exerted by a user generating a torque typically higher than 0.001 N·m, and which moves back to its position of rest when the pressure is released.

On the contrary, the terms "stiff" and "not deformable" are used to describe an element which does not almost bend under the effect of a strength exercised by a user typically generating a torque lower than 0.05 N·m.

The term "sheet" is synonymous with the term "layer".

The Multiple-Compartment Device

As illustrated in FIG. 1, a multiple-compartment device 1 is composed of a closed envelop 2, made of at least two flexible sidewalls 3a and 3b secured together along their peripheral edges 4, defining a sealed perimeter 5 and an internal volume 6, which is divided in at least two distinct compartments 7a and 7b, separated from one another by at least one internal frangible seal 8. According to the present invention, at least one of the compartments 7a contains a composition (A), and the second compartment 7b contains a composition (B).

In other words, the compartment 7a containing the composition (A) is separated from the compartment 7b containing the oxidation composition (B) by the internal frangible seal 8. Compositions (A) and (B) are thus contained in two different compartments 7a and 7b and, cannot commingle together.

Preferably, the multiple-compartment device 1 is divided into two distinct compartments 7a and 7b.

The sealed perimeter 5 has a first end 9, a second end 10, and two opposed sides 11 and 12. Preferably, the sealed perimeter 5 has a width of between 5 to 15 mm.

Each flexible sidewall 3a and 3b is made of at least one sheet of polymeric film. The sheet of polymeric film can be either a single layer or a multilayer polymeric film. The layers of polymeric film may be different in structure.

The length of the sidewalls 3a and 3b preferably ranges from 100 to 200 mm, and more preferentially from 120 to 160 mm.

The width of the sidewalls 3a and 3b preferably ranges from 100 to 200 mm, and more preferentially from 120 to 200 mm.

The length of the first compartment 7a preferably ranges from 5 to 200 mm, and more preferentially from 80 to 150 mm.

The length of the second compartment 7b preferably ranges from 5 to 200 mm, and more preferentially from 80 to 150 mm.

The length of the first compartment 7a may be higher than the length of the second compartment 7b but it is preferably equal to the length of the second compartment 7b.

According to a preferred embodiment, the closed envelop 2 is made of at least one sheet of polymeric film folded back on itself and sealed at its peripheral edges. In other words, according to this particular embodiment, the two flexible sidewalls 3a and 3b are made of the same sheet of polymeric film, which can be either a single layer or a multilayer polymeric film.

Preferably the sheet of polymeric film is a multilayer polymeric film comprising at least two, different or identical, layers of polymeric film. Thus, the sheet of polymeric film has a laminate structure and the layers of polymeric film are superposed on one another.

A second sheet can optionally be made of paper.

The sheet of polymeric film suitable for the present invention is preferably prepared from polyvinyl chloride (PVC), polyesters, polyolefins, polyamides, or polystyrenes.

Examples of polyvinyl chloride (PVC) are vinyl polymers containing vinyl chloride units in their structure, such as copolymers of vinyl chloride with vinyl esters of aliphatic acids, copolymers of vinyl chloride with esters of acrylic or methacrylic acid or with acrylonitrile, copolymers of vinyl chloride with diene bonds and unsaturated dicarboxylic acids or anhydrides thereof, copolymers of vinyl chloride and vinylidene chloride with unsaturated aldehydes, ketones, etc., or polymers and copolymers of vinylidene chloride with vinyl chloride or other polymerizable compounds. The thermoplastics based on vinyl can also be rendered flexible in a manner known per se by means of primary or secondary plasticizers. The PVC sheets can, as the case may be, also be drawn monoaxially (oPVC) or biaxially.

Examples of polyesters are poly(alkylene terephthalate)s or poly(alkylene isophthalate)s having alkyl groups or radicals containing from 2 to 10 carbon atoms or alkyl groups containing from 2 to 10 carbon atoms which are interrupted at least by one —O—, such as, for example, poly(ethylene terephthalate) (PET sheets), poly(propylene terephthalate), poly(butylenes terephthalate) (poly(tetramethylene terephthalate)), poly(decamethylene terephthalate), poly(1,4-cyclohexyldimethylol terephthalate) or poly(ethylene 2,6 naphthalenedicarboxylate), or copolymers of poly(alkylene terephthalate) and poly(alkylene isophthalate), the proportion of isophthalate being, for example, from 1 to 10 mol %, copolymers and terpolymers, and also block polymers and grafted alternative forms of the abovementioned substances. Other appropriate polyesters, such as polyethylene naphthalate, are known in the technical field under the abbreviation PEN.

Other polyesters are copolymers of terephthalic acid and of another polycarboxylic acid with at least one glycol. Copolyesters of terephthalic acid, of ethylene glycol and of an additional glycol are appropriate. Glycol-modified polyesters, which are known in the technical field under the name PETG, are preferred.

Appropriate polyesters are composed of poly(alkylene terephthalate)s having alkyl groups or radicals comprising 2 to 10 carbon atoms and poly(alkylene terephthalate)s having alkyl groups or radicals containing 2 to 10 carbon atoms which are interrupted by 1 or 2 —O—.

Other preferred polyesters are poly(alkylene terephthalate)s having alkyl groups or radicals containing 2 to 4 carbon atoms and preference is very particularly given to poly(ethylene terephthalate)s. These poly(ethylene terephthalate)s also include A-PET, PETP and the PETG mentioned or the G-PET.

Examples of polyolefins are polyethylenes (PE), for example high density polyethylene (HDPE, density of greater than 0.944 g/cm3), medium density polyethylene (MDPE, density of 0.926 to 0.940 g/cm3), linear medium density polyethylene (LMDPE, density of 0.926 to 0.940 g/cm3), low density polyethylene (LDPE, density of 0.910 to 0.925 g/cm3) and linear low density polyethylene (LLDPE, density of 0.916 to 0.925 $g/c_T3$), for example in the form of nonoriented sheets (PE sheet) or monoaxially or biaxially oriented sheets (oPE sheet), polypropylenes (PP), such as axially or biaxially oriented polypropylene (oPP sheet) or cast polypropylene (cPP sheet), amorphous or crystalline polypropylene or blends thereof or atactic or isotactic polypropylene or blends thereof, poly(l-butene), poly(3-methylbutene), poly(4-methylpentene) and copolymers thereof, then polyethylene with vinyl acetate, vinyl alcohol or acrylic acid, such as, for example, ionomer resins, such as copolymers of ethylene, of acrylic acid, of methacrylic acid, of acrylic esters, tetrafluoroethylene or polypropylene, in addition random copolymers, block copolymers or olefin polymer/elastomer blends. The polyolefin materials can also comprise cycloolefins as monomer of a homopolymer or of copolymers.

Preference is given to high density polyethylenes and to polypropylenes, and also to ionomers, for example known under the trade name Surlyn and sold by the company Dupont de Nemours.

Examples of polyamides (PA) for the polymeric film are composed, for example, of polyamide 6, ε-caprolactam homopolymer (polycaprolactam); polyamide 11; polyamide 12, ω-lauryllactam homopolymer (polylauryllactam); polyamide 6,6, homopolycondensate of hexamethylenediamine and of adipic acid (poly(hexamethylene adipamide)); polyamide 6,10, homopolycondensate of hexamethylenediamine and of sebacic acid (poly(hexamethylene sebacamide); polyamide 6,12, homopolycondensate of hexamethylenediamine and of dodecanedioic acid (poly(hexamethylene dodecanamide)) or polyamide 6-3-T, homopolycondensate of trimethylhexamethylenediamine and of terephthalic acid (poly (trimethylhexamethylene terephthalamide)), and blends thereof. The polyamide sheets are drawn monoaxially or biaxially (oPA).

Examples of polystyrenes for the polymeric film are composed, for example, of oriented polystyrene, in particular mono- or biaxially oriented polystyrene, which may be produced by stretching extruded polystyrene film or polystyrene copolymerized with butadiene.

Preferentially, the sheet of polymeric film is chosen from poly(alkylene terephthalate) and polyolefins, and more preferentially from poly(ethylene terephthalate), polyethylene and ionomers, such as copolymer of polyethylene and methacrylic acid, and polystyrene such as oriented polystyrene.

The thickness of polymeric films ranges from 60 μm to 200 μm and preferably from 80 μm to 140 μm.

The internal frangible seal 8, according to the present invention, is comprised in the internal volume 6. Each ends 13 of the internal frangible seal 8 is connected to at least one edge 4 of the sealed perimeter 5. As illustrated in FIG. 1, one of the ends 13 of the internal frangible seal 8 is connected to the first end 9, while the other end 13 of the internal frangible seal 8 is connected to the second end 10 of the sealed perimeter 5.

The expressions "seal" or "sealed perimeter", according to the present invention, refer to a definitive bond between two sheets of polymeric film or between two parts of a sheet folded back on itself. This seal can be obtained fusing and/or mixing together the two sheets or the two parts. In other words, the seal between the two sheets or the two parts cannot be opened without damaging the walls formed by the two sheets or by the two parts.

The expression "frangible seal", according to the present invention, refers to a non definitive bound between two sheets of polymeric film. In other words, the frangible seal can be opened without damaging the walls formed by the two sheets.

The internal frangible seal 8 is formed by heat-sealing or ultrasonic-sealing process the internal layers of the sidewalls 3a and 3b. In other words, the internal parts of polymeric film(s) forming the sidewalls 3a and 3b are sealed together in order to create the internal frangible seal 8.

The internal frangible seal 8 provides impermeability between the two compartments 7a and 7b, avoiding the composition (A) contained in one of the compartment 7a to mix with the oxidation composition (B) contained in the second compartment 7b.

However, when a consumer applies a pressure to the closed envelop 2 in the region of a compartment (first compartment 7a or second compartment 7b), the internal frangible seal 8 breaks under the force of the pressure transmitted by the composition contained in the compartment to the frangible seal. The compositions (A) and (B) contained in both compartments can pass from one compartment to the other through the broken seal, and can thus mix together.

The internal frangible seal thus requires two conflicting performance. On the first hand, the internal frangible seal provides a relatively strong resistance to a force generated during normal storage or handling, in order to avoid inadvertent rupture of the seal. And on the second hand, the internal frangible seal shall be completely broken upon user activation, in order to avoid restriction of the flow path between the two compartments, inducing thus an unsatisfactory mixing of compositions (A) and (B).

The force pressure to apply in order to break the internal membrane in between the two compartments ranges from 0.5 kg/cm2 to 3 kg/cm2.

The multiple-compartment device 1 may also comprise an opening means, for example by way of tearing or cutting with a pair of scissors. According to a preferred embodiment, the opening means is a pre-cut line 14 parallel to the first end 9 of the sealed perimeter 5, as illustrated in FIG. 1.

The pre-cut line 14 can be produced by laser, and can then be torn easily without a tool.

FIG. 2 illustrates a variant embodiment of a multiple-compartment device 1 in the form of a stand-up device. The respective elements comprising this embodiment are identified by using the corresponding reference numbers used for the description of the multiple-compartment device in FIG. 1.

This particular embodiment differs from the device disclosed in FIG. 1 in that the second end 10 of the sealed perimeter 5 has a bottom 15 and involves a folded gusset structure 16 allowing the multiple-compartment device 1 to be freestanding.

At the first end 9, as well as at the two opposed sides 11 and 12, the sheet of polymeric film can be sealed without gusset. Such an embodiment may involve a more complex sealed perimeter 5 to create the gusset 16 and the bottom 15.

As indicated previously, the compartment 7a of the multi-compartment device according to the present invention contains a composition A.

Composition (A)

Oxidation Dye Precursors

Composition A comprises at least an oxidation dye precursor. Oxidation dye precursors may be selected from oxidation bases and couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ- dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino aminotoluene, 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred. Even more preferably mention may be made of para-phenylenediamine.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(3-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido aminophenol, and the addition salts thereof.

Among the heterocyclic bases, mention may be made, by way of example, of pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases of use in the present invention are the 3-aminopyrazolo[1,5-a]pyridine oxidation bases or the addition salts thereof described, for example, in Patent Application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, 2-[(3-aminopyrazolo[1,5-a]pyridin-2-yl)oxy]ethanol and addition salts thereof.

Among the pyrimidine derivatives that may be mentioned are the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, and tautomeric forms thereof, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used.

As heterocyclic bases, use will preferably be made of 4,5-diamino-1-(β-hydroxyethyl)pyrazole and/or 2,3-diamino-6,7-dihydro-1H,5H-pyrazolo[1,2-a]pyrazol one and/or 2-[(3-aminopyrazolo[1,5-a]pyridin-2-yl)oxy]ethanol and/or a salt thereof.

More specifically the oxidation bases are chosen from paraphenylenediamines and para-aminophenols, preferably para-phenylenediamine and/or para-aminophenol.

Among the couplers that may be used in the composition of the invention, mention may be made especially of meta-phenylenediamines, meta-aminophenols, meta-diphenols, naphthalene-based couplers and heterocyclic couplers, and also the addition salts thereof with an acid, and mixtures thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

More specifically, composition of the invention contains couplers chosen from meta-phenylenediamines, meta-aminophenols such as 2,4-diaminophenoxyethanol, 4-amino-2-hydroxytoluene, 2-methyl-5-hydroxyethylaminophenol, and a mixture thereof.

The addition salts of the oxidation bases and couplers are especially chosen from the addition salts with an acid such as the hydrochlorides, hydrobromides, sulfates, citrates, succinates, tartrates, lactates, tosylates, benzenesulfonates, phosphates and acetates.

According to one embodiment, the oxidation dye precursors are selected from para-phenylenediamine, para-aminophenol, m-aminophenol, 2,4-diaminophenoxyethanol, 4-amino hydroxytoluene, 2-methyl-5-hydroxyethylaminophenol, and a mixture thereof.

The oxidation base(s) are each generally present in an amount of from 0.0001% to 10% by weight relative to the total weight of the composition A, and preferably from 0.005% to 7% by weight, more preferably from 0.1% to 4% by weight relative to the total weight of composition A.

The coupler(s) each generally represent from 0.0001% to 10% by weight relative to the total weight of composition A, and preferably from 0.005% to 7% by weight, more preferably from 0.1% to 4% by weight relative to the total weight of composition A.

Anionic Surfactant

Composition (A) further comprises at least one anionic surfactant (also called "surface-active agent").

The term "anionic surfactant" is intended to mean a surfactant comprising, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

The anionic surfactants may be sulfate, sulfonate and/or carboxylic (or carboxylate) surfactants. Needless to say, a mixture of these surfactants may be used.

It is understood in the present description that:
the carboxylate anionic surfactants comprise at least one carboxylic or carboxylate function (—COOH or —COO—) and may optionally also comprise one or more sulfate and/or sulfonate functions;
the sulfonate anionic surfactants comprise at least one sulfonate function (—SO3H or —SO3-) and may optionally also comprise one or more sulfate functions, but do not comprise any carboxylate functions; and
the sulfate anionic surfactants comprise at least one sulfate function but do not comprise any carboxylate or sulfonate functions.

The carboxylic anionic surfactants that may be used thus comprise at least one carboxylic or carboxylate function (—COOH or —COO—).

They can be chosen from the following compounds: acylglycinates, acyllactylates, acylsarcosinates, acylglutamates, alkyl ether carboxylic acids, alkyl(C6-30 aryl) ether carboxylic acids, alkyl-D-galactoside-uronic acids, alkylamido ether carboxylic acids; and also the salts of these compounds; the alkyl and/or acyl groups of these compounds comprising from 6 to 30 carbon atoms, in particular from 12 to 28, better still from 14 to 24 or even from 16 to 22 carbon atoms; the aryl group preferably denoting a phenyl or benzyl group; these compounds possibly being polyoxyalkylenated, in particular polyoxyethylenated, and then preferably comprising from 1 to 50 ethylene oxide units, better still from 2 to 10 ethylene oxide units.

Use may also be made of the C6-C24 alkyl monoesters of polyglycoside-polycarboxylic acids, such as C6-C24 alkyl polyglycoside-citrates, C6-C24 alkyl poly-glycoside-tartrates and C6-C24 alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene ox-ide groups, such as the compounds sold by the company Kao under the name Akypo.

The polyoxyalkylenated alkyl(amido) ether carboxylic acids that may be used are preferably chosen from those of formula (1):

R1'-(OC$_2$H$_4$)$_{n'}$—OCH$_2$COOA (1)

in which:
R1' represents a linear or branched C6-C24 alkyl or alkenyl radical, a (C8-C9)alkylphenyl radical, an R2'CONH—CH$_2$—CH$_2$— radical with R2' denoting a linear or branched C9-C21 alkyl or alkenyl radical; preferably R1' is a C8-C20, preferably C8-C18, alkyl radical and aryl preferably denotes phenyl,
n' is an integer or decimal number (average value) ranging from 2 to 24 and preferably from 2 to 10,
A denotes H, ammonium, Na, K, Li, Mg or a monoethanolamine or triethanolamine residue.

It is also possible to use mixtures of compounds of formula (1), in particular mixtures of compounds containing different R1' groups.

The polyoxyalkylenated alkyl(amido) ether carboxylic acids that are particularly preferred are those of formula (1) in which:
R1' denotes a linear or branched C8-C22, in particular C10-C16 or even C12-C14 alkyl radical, or alternatively a (C8-C9)alkylphenyl radical;

A denotes a hydrogen or sodium atom, and n' ranges from 2 to 20, preferably from 2 to 10.

Even more preferentially, use is made of compounds of formula (1) in which R1' denotes a C12 alkyl radical, A denotes a hydrogen or sodium atom and n' ranges from 2 to 10.

Preferentially, the carboxylic anionic surfactants are chosen, alone or as a mixture, from:

acylglutamates, in particular of C6-C24 or even C12-C20, such as stearoylglutamates, and in particular disodium stearoylglutamate;

acylsarcosinates, in particular of C6-C24 or even C12-C20, such as palmitoylsarcosinates, and in particular sodium palmitoylsarcosinate;

acyllactylates, in particular of C12-C28 or even C14-C24, such as behenoyllactylates, and in particular sodium behenoyllactylate;

C6-C24 and in particular C12-C20 acylglycinates;

(C6-C24)alkyl ether carboxylates, and in particular (C12-C20)alkyl ether carboxylates; in particular those comprising from 2 to 50 ethylene oxide groups;

polyoxyalkylenated (C6-C24)alkylamido ether carboxylic acids, in particular those comprising from 2 to 50 ethylene oxide groups;

in particular in acid form or in the form of alkali metal or alkaline-earth metal, ammonium or amino alcohol salts.

The sulfonate anionic surfactants that may be used comprise at least one sulfonate function ($-SO_3H$ or $-SO_3-$). They may be chosen from the following com-pounds: alkylsulfonates, alkyl ether sulfonates, alkylamidesulfonates, alkylaryl-sulfonates, α-olefin sulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds;

the alkyl groups of these compounds comprising from 6 to 30 carbon atoms, in particular from 12 to 28, better still from 14 to 24 or even from 16 to 22 carbon atoms; the aryl group preferably denoting a phenyl or benzyl group;

these compounds possibly being polyoxyalkylenated, in particular polyoxyethylenated, and then preferably comprising from 1 to 50 ethylene oxide units and better still from 2 to 10 ethylene oxide units.

Preferentially, the sulfonate anionic surfactants are chosen, alone or as a mixture, from:

C6-C24 and in particular C12-C20 alkylsulfosuccinates, in particular laurylsulfosuccinates;

C6-C24 and in particular C12-C20 alkyl ether sulfosuccinates;

(C6-C24)acylisethionates and preferably (C12-C18)acylisethionates;

in particular in the form of alkali metal or alkaline-earth metal, ammonium or amino alcohol salts.

The sulfate anionic surfactants that may be used comprise at least one sulfate function ($-OSO_3H$ or $-OSO_3-$).

They may be chosen from the following compounds: alkyl sulfates, alkyl ether sulfates, alkylamido ether sulfates, alkylaryl polyether sulfates, monoglyceride sulfates; and also the salts of these compounds;

the alkyl groups of these compounds comprising from 6 to 30 carbon atoms, in particular from 8 to 28, better still from 10 to 24 or even from 12 to 22 carbon atoms; the aryl group preferably denoting a phenyl or benzyl group;

these compounds possibly being polyoxyalkylenated, in particular polyoxyethylenated, and then preferably comprising from 1 to 50 ethylene oxide units and better still from 2 to 10 ethylene oxide units.

Preferentially, the sulfate anionic surfactants are chosen, alone or as a mixture, from:

alkyl sulfates, in particular of C6-C24 or even C12-C20, alkyl ether sulfates, in particular of C6-C24 or even C12-C20, preferably comprising from 1 to 20 ethylene oxide units;

in particular in the form of alkali metal or alkaline-earth metal, ammonium or amino alcohol salts.

When the anionic surfactant is in salt form, said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used. Anionic surfactant agent is understood to mean an amphiphilic compound in which the hydrophobic part carries an anionic hydrophilic group with a cationic counterion which is generally metallic (alkali metal, such as Na or K) or ammonium; the hydrophilic group is thus polar and capable of dissociating to give anions in aqueous solution.

More particularly the anionic part of the anionic surfactant is belonging to the group chosen from: $C(O)OH$, $-C(O)O^-$, $-SO_3H$, $-S(O)_2O^-$, $-OS(O)_2OH$, $-OS(O)_2O^-$, $-P(O)OH_2$, $-P(O)_2O^-$, $-P(O)O_2-$, $-P(OH)_2$, $=P(O)OH$, $-P(OH)O^-$, $=P(O)O^-$, $=POH$, $=PO^-$, the anionic part comprising a cationic counter anion such as alkali or alkaline earth metal or organic cationic counter anion such as ammonium. Mention may be made, as anionic surface-active agents, of surface-active agents comprising carboxylate, sulfate, sulfonate, sulfoacetate, sulfosuccinate, phosphate, isethionate, sarcosinate, glutamate, lactylate or taurate anionic groups, salts of fatty acids, salts of galacto iduronic acids, salts of ether carboxylic acids and their mixtures.

More particularly, the anionic surface-active agent or agents according to the invention are chosen from:

($C_6$-$C_{30}$)alkyl sulfates, ($C_6$-$C_{30}$)alkyl ether sulfates, ($C_6$-$C_{30}$)alkylamido ether sulfates, alkylaryl polyether sulfates or monoglyceride sulfates;

($C_6$-$C_{30}$)alkyl sulfonates, ($C_6$-$C_{30}$)alkylamidesulfonates, ($C_6$-$C_{30}$)alkylaryl sulfonates, α-olefin sulfonates, paraffin sulfonates;

($C_6$-$C_{30}$)alkyl phosphates;

($C_6$-$C_{30}$)alkyl sulfosuccinates, ($C_6$-$C_{30}$)alkyl ether sulfosuccinates or ($C_6$-$C_{30}$)alkylamido sulfosuccinates;

($C_6$-$C_{30}$)alkyl sulfoacetates;

($C_6$-$C_{24}$)acylsarcosinates;

($C_6$-$C_{24}$)acylglutamates;

($C_6$-$C_{30}$)alkylpolyglycoside carboxylic ethers; ($C_6$-$C_{30}$)alkylpolyglycoside sulfosuccinates;

($C_6$-$C_{30}$)alkyl sulfosuccinamates;

($C_6$-$C_{24}$)acyl isethionates;

N—[($C_6$-$C_{24}$)acyl]taurates;

salts of fatty acids;

($C_8$-$C_{20}$)acyl lactylates;

salts of ($C_6$-$C_{30}$)alkyl-D-galactosiduronic acids;

salts of ($C_6$-$C_{30}$)alkyl polyoxyalkylenated ether carboxylic acids, of ($C_6$-$C_{30}$)alkylaryl polyoxyalkylenated ether carboxylic acids or of ($C_6$-$C_{30}$)alkylamido polyoxyalkylenated ether carboxylic acids;

and their mixtures.

These anionic surface-active agents are advantageously found in the form of salts in the composition according to the invention, in particular of salts of alkali metals, such as sodium; of alkaline earth metals, such as, for example, magnesium; of ammonium salts; of amine salts; or of aminoalcohol salts. They might also, according to the conditions, occur in their acid form.

It should be noted that the alkyl or acyl radicals of these various compounds preferably comprise from 12 to 20 carbon atoms. Preferably, the aryl radical denotes a phenyl or benzyl group.

Furthermore, the polyoxyalkylenated anionic surface-active agents preferably comprise from 2 to 50 alkylene oxide groups, in particular ethylene oxide groups.

In accordance with a preferred embodiment of the invention, the anionic surface-active agent is chosen from salts of fatty acids or sulfates surfactant.

Preferably, the anionic surfactants of the invention are sulfates, more specifically are chosen from ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates and monoglyceride sulfates, their salts such as alkali salts, such as sodium, and their mixtures.

More preferably the anionic surfactants of the invention are chosen from ($C_6$-$C_{30}$)alkyl sulfates, ($C_6$-$C_{30}$)alkyl ether sulfates, particularly ($C_6$-$C_{30}$)alkyl ether sulfates such as lauryl ether sulfate, their salts, such as sodium laureth sulfate.

Advantageously, the total content of anionic surface-active agent(s) represents from 0.1 to 10% by weight, preferably from 0.5 to 8.0% by weight, more preferably from 0.75% to 5.0% by weight, most preferably from 1.0% to 3.0% by weight relative to the total weight of composition (A).

Amphoteric Surfactant Chosen from Betaine

Composition (A) further comprises one or more amphoteric surfactant(s) chosen from betaines.

Preferably, the amphoteric surfactant is chosen from (C8-C20)alkylbetaines and (C8-C20alkyl)amido(C3-C8alkyl) betaines, and particularly from cocoylbetaine, and cocoylamidopropylbetaine, or mixtures thereof.

More preferentially, the amphoteric surfactant(s) are chosen from ((C8-C20 alkyl)amido(C2-C8 alkyl)betaines, and even more preferably cocoylamidopropylbetaine.

Advantageously, the total content of amphoteric surfactant(s) chosen from betaines represents from 0.1 to 10% by weight, preferably from 0.5 to 8.0% by weight, more preferably from 0.75% to 5.0% by weight, most preferably from 1.0% to 4.0% by weight relative to the total weight of composition (A).

Anionic Associative Polymer

Composition (A) may further comprise at least one anionic associative polymer.

Within the meaning of the present invention, the term "polymer" is understood to mean any compound resulting from the polymerization by polycondensation or from the radical polymerization of monomers, at least one of which is other than an alkylene oxide and than a monofunctional compound of formula RX, R denoting an optionally hydroxylated $C_{10}$-$C_{30}$ alkyl or alkenyl group and X denoting a carboxylic acid, amine, amide, hydroxyl or ester group. All the compounds resulting solely from the simple condensation of an alkylene oxide with a fatty alcohol, a fatty ester, a fatty acid, a fatty amide or a fatty amine are in particular excluded.

Within the meaning of the present invention, the term "associative polymer" is understood to mean an amphiphilic polymer capable, in an aqueous medium, of reversibly associating with itself or with other molecules. It generally comprises, in its chemical structure, at least one hydrophilic region or group and at least one hydrophobic region or group.

The term "hydrophobic group" is understood to mean a group or a polymer comprising a saturated or unsaturated and linear or branched hydrocarbon chain. When it denotes a hydrocarbon group, the hydrophobic group comprises at least 8 carbon atoms, preferably from 10 to 30 carbon atoms, in particular from 12 to 30 carbon atoms and preferentially from 18 to 30 carbon atoms. Preferentially, the hydrocarbon hydrophobic group originates from a monofunctional compound. By way of example, the hydrophobic group can result from a fatty alcohol, such as stearyl alcohol, dodecyl alcohol or decyl alcohol, or else from a polyalkylenated fatty alcohol, such as Steareth-100. It can also denote a hydrocarbon polymer, such as, for example, polybutadiene.

Mention may be made, among the associative polymers of anionic type, of:

(1) those comprising at least one hydrophilic unit and at least one fatty-chain allyl ether unit, more particularly those for which the hydrophilic unit is composed of an ethylenic unsaturated anionic monomer, more particularly still of a vinylcarboxylic acid and very particularly of an acrylic acid or a methacrylic acid or the mixtures of these, and the fatty-chain allyl ether unit of which corresponds to the monomer of following formula (III):

$CH_2=CR'CH_2OB_nR$     (III)

in which R' denotes H or $CH_3$, B denotes the ethyleneoxy group, n is zero or denotes an integer ranging from 1 to 100 and R denotes a hydrocarbon group chosen from alkyl, arylalkyl, aryl, alkylaryl or cycloalkyl groups comprising from 8 to 30 carbon atoms, preferably from 10 to 24 carbon atoms and more particularly still from 12 to 18 carbon atoms.

Within the meaning of the present invention, the term "fatty chain" is understood to mean a linear or branched alkyl or alkenyl chain comprising at least 8 carbon atoms, preferably from 8 to 30 carbon atoms and better still from 10 to 22 carbon atoms.

A unit of formula (III) more particularly preferred is a unit in which R' denotes H, n is equal to 10 and R denotes a stearyl ($C_{18}$) group.

Anionic associative polymers of this type are described and prepared, according to an emulsion polymerization process in Patent EP-0 216 479.

Preference is particularly given, among these anionic associative polymers, according to the invention, to the polymers formed from 20% to 60% by weight of acrylic acid and/or of methacrylic acid, from 5% to 60% by weight of C1-C4 alkyl (meth)acrylates, from 2% to 50% by weight of fatty-chain allyl ether of formula (III) and from 0% to 1% by weight of a crosslinking agent which is a well-known copolymerizable polyethylenic unsaturated monomer, such as diallyl phthalate, allyl (meth)acrylate, divinylbenzene, (poly)ethylene glycol dimethacrylate or methylenebisacrylamide.

Preference is very particularly given, among the latter polymers, to crosslinked terpolymers of methacrylic acid, of ethyl acrylate, of stearyl alcohol ether of polyethylene glycol (10 mol of ethylene oxide (EO)) (Steareth-10), in particular those sold by Ciba under the names Salcare SC 80 and Salcare SC 90, which are aqueous emulsions comprising 30% by weight of a crosslinked terpolymer of methacrylic acid, of ethyl acrylate and of Steareth-10 allyl ether (40/50/10).

(2) those comprising at least one hydrophilic unit of unsaturated olefinic carboxylic acid type and at least one hydrophobic unit of (C10-C30)alkyl ester of unsaturated carboxylic acid type.

These polymers are preferably chosen from those for which the hydrophilic unit of unsaturated olefinic carboxylic acid type corresponds to the monomer of formula (IV) below:

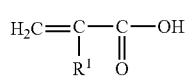  (IV)

in which $R^1$ denotes H or $CH_3$ or $C_2H_5$, which corresponds to acrylic acid, methacrylic acid or ethacrylic acid units, and for which the hydrophobic unit of $(C_{10}\text{-}C_{30})$alkyl ester of unsaturated carboxylic acid type corresponds to the monomer of following formula (V):

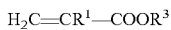  (V)

in which $R^1$ denotes H or $CH_3$ or $C_2H_5$, which corresponds to acrylic acid, methacrylic acid or ethacrylic acid units, and preferably H (acrylate units) or $CH_3$ (methacrylate units), and $R^3$ denotes a $C_{10}\text{-}C_{30}$ and preferably $C_{12}\text{-}C_{22}$ alkyl group.

$(C_{10}\text{-}C_{30})$Alkyl esters of unsaturated carboxylic acids in accordance with the invention comprise, for example, lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate and dodecyl methacrylate.

Anionic polymers of this type are, for example, described and prepared according to U.S. Pat. Nos. 3,915,921 and 4,509,949.

Use will more particularly be made, among anionic associative polymers of this type, of polymers formed from a mixture of monomers comprising:
(i) essentially acrylic acid,
(ii) an ester of formula (V) described above in which $R^1$ denotes H or $CH_3$ and $R^3$ denotes an alkyl group having from 12 to 22 carbon atoms, and
(iii) a crosslinking agent, which is a well-known copolymerizable polyethylenic unsaturated monomer, such as diallyl phthalate, allyl (meth)acrylate, divinylbenzene, (poly)ethylene glycol dimethacrylate or methylenebisacrylamide.

Use will more particularly be made, among anionic associative polymers of this type, of those composed of 95% to 60% by weight of acrylic acid (hydrophilic unit), 4% to 40% by weight of $C_{10}\text{-}C_{30}$ alkyl acrylate (hydrophobic unit) and 0% to 6% by weight of crosslinking polymerizable monomer, or else of those composed of 98% to 96% by weight of acrylic acid (hydrophilic unit), 1% to 4% by weight of $C_{10}\text{-}C_{30}$ alkyl acrylate (hydrophobic unit) and 0.1% to 0.6% by weight of crosslinking polymerizable monomer such as those described above.

Preference is very particularly given, among the above said polymers, according to the present invention, to the products sold by Lubrizol under the trade names Pemulen TR1, Pemulen TR2, Carbopol 1382, Carbopol ETD 2020, Carbopol Ultrez 20, Carbopol Ultrez 21, having the INCI name Acrylates/$C_{10\text{-}30}$ alkyl acrylate crosspolymer, and more preferably still Pemulen TR1 and Carbopol 1382.

(3) maleic anhydride/$C_{30}\text{-}C_{38}$ α-olefin/alkyl maleate terpolymers, such as the product maleic anhydride/$C_{30}\text{-}C_{38}$ α-olefin/isopropyl maleate copolymer sold under the name Performa V 1608 by Newphase Technologies.

(4) acrylic terpolymers comprising:
(a) approximately 20% to 70% by weight of a carboxylic acid having α,β-monoethylenic unsaturation,
(b) approximately 20% a 80% by weight of a non-surfactant monomer having α,β-monoethylenic unsaturation other than (a),
(c) approximately 0.5% to 60% by weight of a nonionic monourethane which is the reaction product of a monohydric surfactant with a monoisocyanate having monoethylenic unsaturation, such as those described in Patent Application EP-A-0 173 109 and more particularly that described in Example 3, namely a methacrylic acid/methyl acrylate/ethoxylated (40 EO) behenyl alcohol dimethyl-meta-isopropenyl-benzyl isocyanate terpolymer, as a 25% by weight aqueous dispersion. Mention may be made, as example of this type of compound, of Viscophobe DB 1000, sold by Amerchol (Dow Chemical), with the INCI name Polyacrylate-3.

(5) copolymers comprising, among their monomers, a carboxylic acid having α,β-monoethylenic unsaturation and an ester of carboxylic acid having α,β-monoethylenic unsaturation and of an oxyalkylenated fatty alcohol. Preferentially, these compounds also comprise, as monomer, an ester of carboxylic acid having α,β-monoethylenic unsaturation and of $C_1\text{-}C_4$ alcohol.

The anionic associative polymer of the present invention is preferably chosen from copolymers comprising, among their monomers, a carboxylic acid having α,β-monoethylenic unsaturation and an ester of carboxylic acid having α,β-monoethylenic unsaturation and of an oxyalkylenated fatty alcohol.

Preferably, the anionic associative polymer comes from the copolymerization between 1) and 2):
1) at least one ethylenically unsaturated mono or dicarboxylic acid monomer substituted by at least one, linear or branched, $(C_1\text{-}C_{10})$alkyl group; and
2) at least one associative monomer which is an ester of formula (I):

  (I)

Formula (I) wherein:
A represents a ethylenically unsaturated acyclic residue, optionally containing an additional carboxylic group or it salt, wherein said additional carboxylic group may be esterified with a linear or branched $(C_1\text{-}C_{20})$alkyl group;
$R^a$ represents an alkyl a linear or branched $(C_1\text{-}C_{30})$alkyl group, alkylaryl or arylalkyl group having from 1 to 30 carbon atoms wherein the alkyl group is linear or branched, preferably $R^a$ represents $(C_1\text{-}C_{20})$alkyl group, alkylphenyl or phenylalkyl group having from 1 to 20 carbon atoms wherein the alkyl group is linear or branched;
Alk represents a linear or branched $(C_1\text{-}C_6)$alkylene group, particularly Alk represents —$CH_2$—$CH(R^b)$— wherein $R^b$ represents a hydrogen atom, or a $(C_1\text{-}C_4)$ alkyl group such as methyl or ethyl group;
z is an integer comprised inclusively between 0 and 50;
w is an integer comprised inclusively between 0 and 30;

with the proviso that (I) contains at least one carboxyl group C(O)OH, or C(O)O-Q⁺ wherein Q⁺ represents cation chosen from an alkali metal, an alkaline earth metal, or ammonium;

By polymerization of 1) and 2), it must be understood a copolymerisation between at least one monomer 1) with at least one monomer 2).

According to an embodiment of the invention the copolymer comes from the polymerization between at least one ethylenically unsaturated mono or dicarboxylic acid monomer (1a) and at least one associative monomer which is an ester of formula (I) as defined herein before or (2a):

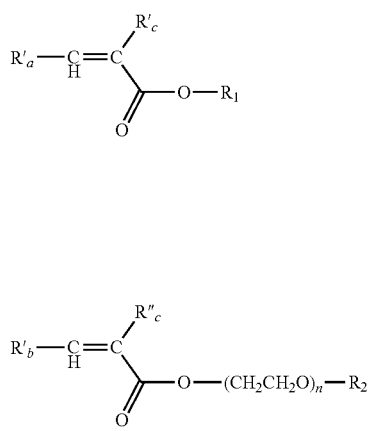

(1a)

(2a)

Formulas (1a) and (2a) wherein:

$R'_a$ and $R'_b$, identical or different, represent a hydrogen atom, or a linear or branched ($C_1$-$C_6$)alkyl group, preferably $R'_a$ and $R'_b$ represent hydrogen atom;

$R'_c$ and $R''_c$, identical or different, represent a hydrogen atom, or a linear or branched ($C_1$-$C_6$)alkyl group, a C(O)OX group, or a -alk-C(O)OX group wherein X represents a atom, an alkali metal, alkaline earth metal, or ammonium and -alk- represents a ($C_1$-$C_6$)alkylene group such as methylene group, preferably $R'_c$ and/or $R''_c$ represent a hydrogen atom or a methyl group;

$R_1$ represents a hydrogen atom, an alkali metal, alkaline earth metal, or a ($C_1$-$C_6$)alkyl group;

$R_2$ represents a, linear or branched, ($C_6$-$C_{40}$)alkyl group, preferably a ($C_{10}$-$C_{30}$)alkyl group; n is an integer comprised inclusively between 5 and 100, particularly between 10 and 50, more particularly between 20 and 40, preferably between 20 and 30 such as 25;

with the proviso that (1a) or (2a) contain at least one carboxyl group C(O)OH, or C(O)O-Q⁺ wherein Q⁺ represents cation chosen from an alkali metal, alkaline earth metal or ammonium.

Particularly $R'_a$, $R'_b$ represent a hydrogen atom and $R'_c$, and $R''_c$ represent a hydrogen atom or a methyl group and $R_1$ represents a hydrogen atom, an alkali metal, alkaline earth metal.

According to another variant $R'_a$, $R'_b$, and $R'_c$ represent a hydrogen atom and $R''_c$ represents a group -alk-C(O)OX such as —CH2-C(O)OX wherein X is as defined herein before.

According to a particular embodiment of the invention, the polymer i) contains units (Ia) and/or (I'a):

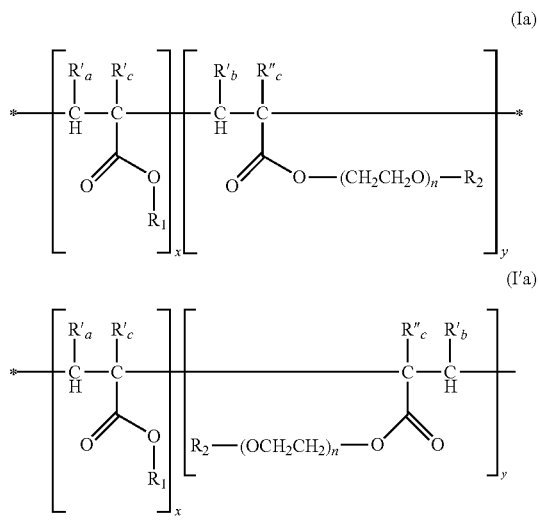

wherein $R'_a$, $R'_b$, $R'_c$, $R''_c$ are as defined herein before;

x represents an integer, preferably more than 100, more preferably between 100 and 10000;

y represents an integer, preferably more than 100, more preferably between 100 and 10000;

and x+y represents an integer, preferably >200, more preferably between 200 and 20000.

According to a preferred embodiment, the anionic associative polymer of the present invention has a molecular weight of more than 100000, preferably between 200000 and 8000000.

According to a preferred embodiment, in formula (Ia) and (I'a), $R_1$ represents a hydrogen atom, an alkali metal, or an alkaline earth metal.

As example of copolymer (1a)/(2a) as defined herein before, usable in the invention, we may mention: acrylates/palmeth-25 acrylate copolymer, such as the products commercially available from 3V under the trade name Synthalen® W2000, acrylates/beheneth-25 methacrylate copolymer, such as the products commercially available from Lubrizol under the trade name Novethix® L-10, acrylates/steareth-20 methacrylate copolymer, such as the products commercially available from Rohm and Haas (Dow Chemical) under the trade name Aculyn™ 22 polymer, acrylates/steareth-20 itaconate copolymer, such as the products commercially available from AkzoNobel under the trade name Structure 2001, acrylates/ceteth-20 itaconate copolymer, such as the products commercially available from AkzoNobel under the trade name Structure 3001, acrylates/ceteth-20 methacrylate copolymer, acrylate/beheneth-25 itaconate copolymer, acrylate/palmeth-25 methacrylates copolymer, acrylate/steareth-50 acrylate copolymer, acrylates/palmeth-25 itaconate copolymer, such as the products commercially available from Sigma-3V under the trade name Polygel W 40, and mixtures thereof.

Among the above said polymers acrylates/beheneth-25 methacrylate copolymer, such as the products commercially available from Lubrizol under the trade name Novethix® L-10 is specially preferred.

When present in composition (A), the anionic associative polymers described above are preferably used in a total amount which may range from 0.01 to 5% by weight, preferably from 0.05 to 3% by weight, more preferably from 0.075 to 2% by weight, most preferably from 0.1 to 1.5% by weight relative to the total weight of composition (A).

Anionic Non Associative Polymer

Composition (A) may further comprise an anionic non associative polymer.

Anionic non associative polymers contains hydrophilic units of unsaturated olefinic carboxylic acid, and potentially in the presence of at least one cross-linking agent.

The anionic non associative polymer is preferably chosen from those obtained from at least one monomer of formula (3) below:

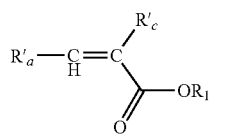
(3)

Formula (3) in which $R'_a$ and $R'_c$ and $R_1$ are as defined herein before, more specifically $R'_a$ represents a hydrogen atom, $R'_c$ represents a hydrogen atom, a methyl group or a ethyl group with the proviso that at least one monomer is such that $R_1$ represents a hydrogen atom, an alkali metal, alkaline earth metal. According to a particular embodiment, the polymer is a polymer obtained from monomer (3) as previously defined with $R_1$ represents a hydrogen atom, an alkali metal, alkaline earth metal.

According to another embodiment, the anionic non associative polymer is a homopolymer obtained from acrylic acid monomers or methacrylic acid monomers, preferably acrylic acid monomers.

According to the present invention, the anionic non associative polymer can be cross linked. By crosslinking agent it must be understood an agent able to make links between molecular chains to form a three-dimensional network of connected molecules (co) or (homo)polymers.

The said crosslinking agent is a monomer more specifically containing at least one group ethylenyl or allylether group as the following formula (4) or (5):

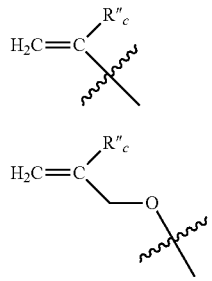

(4)

(5)

formula (4) or (5) wherein $R''_c$ is as defined herein before, more particularly represent H or methyl group, with at least one other polymerizable group whose unsaturated bonds are not conjugated to each other. Mentions may be made of derivatives of ethylene glycol di(meth)acrylate such as ethylene glycol diacrylate, di(ethylene glycol) diacrylate, tetra(ethylene glycol) diacrylate, ethylene glycol dimethacrylate, di(ethylene glycol) dimethacrylate, tri(ethylene glycol) dimethacrylate, derivatives of methylenebisacrylamide such as N,N-methylenebisacrylamide, N,N-methylenebisacrylamide, N,N-(1,2-dihydroxyethylene) bisacrylamide, formaldehyde-free crosslinking agent such as N-(1-hydroxy-2,2-dimethoxyethyl)acrylamide, and divinylbenzene, and (poly)allylether.

Preferably the monomers (3) are polymerized in a presence of cross-linking agent especially in a presence of (poly)allyl ethers in particular, (poly)allyl sucrose and (poly) allyl pentaerylthritol such as carbomer which correspond to a homopolymer of acrylic acid crosslinked with an allyl ether of pentaerythritol, an allyl ether of sucrose, or an allyl ether of propylene.

The anionic non associative polymer can be selected from Carbomer. Carbomer is a crosslinked homopolymer of acrylic. This Carbomer is for example sold under the trade name Carbopol® 940, Carbopol® 941, Carbopol® 980, Carbopol® 981, preferably Carbopol® 980.

When present in composition (A), the anionic non associative polymers are preferably used in a total amount which may range from 0.01 to 2.5% by weight, preferably from 0.05 to 2% by weight, more preferably from 0.1 to 1.8% by weight, most preferably from 0.5 to 1.5% by weight relative to the total weight of composition (A).

Alkaline Agent

Composition (A) may further comprise at least an alkaline agent(s). This agent may be chosen from mineral or organic or hybrid alkaline agents, or mixtures thereof.

The mineral alkaline agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a pKb at 25° C. of less than 12, preferably less than 10 and even more advantageously less than 6. It should be noted that it is the pKb corresponding to the function of highest basicity.

Hybrid compounds that may be mentioned include the salts of the amines mentioned previously with acids such as carbonic acid or hydrochloric acid.

The organic alkaline agent(s) are chosen, for example, from alkanolamines, oxyethylenated and/or oxypropylenated ethylenediamines, amino acids and the compounds of formula below:

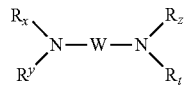

in which W is a $C_1$-$C_6$ alkylene residue optionally substituted with a hydroxyl group or a $C_1$-$C_6$ alkyl radical; $R_x$, $R_y$, $R_z$ and $R_t$, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for performing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane, preferably monoethanolamine.

Composition (A) of the invention preferably contains one or more alkanolamines. More preferentially still, the organic amine is monoethanolamine.

Advantageously, composition (A) according to the invention further has a total content of alkaline agent(s) ranging from 0.01% to 30% by weight, preferably from 0.1% to 20% by weight and better still from 1% to 10% by weight, and even more preferably from 2% to 8% by weight relative to the weight of said composition (A).

Preferably, composition (A) may comprise water in an amount ranging from 40% to 98% by weight, preferably from 60% to 95% by weight and better still from 80% to 90% by weight of the total weight of composition (A).

Preferably, composition (A) is free of oxidizing agent.

As indicated previously, the compartment (7b) of the multi-compartment device according to the present invention contains an oxidizing composition (B).

Composition (B)

Oxidizing Agent

The oxidizing composition (B) comprises at least an oxidizing agent.

The oxidizing agents are especially chemical oxidizing agents, in other word it is different from the oxygen of the air. Preferably the oxidizing agent is chosen, for example, from hydrogen peroxide, urea peroxide, alkali metal bromates or ferricyanides, peroxygenated salts, for instance persulfates, perborates, peracids, and precursors thereof and percarbonates of alkali metals or of alkaline-earth metals. Advantageously, the oxidizing agent is hydrogen peroxide.

The total content of oxidizing agent(s) more particularly represents from 0.1% to 20% by weight and preferably from 1% to 12% by weight relative to the weight of composition (B).

Preferably, composition (B) may comprise water in an amount ranging from 40% to 98% by weight, preferably from 60% to 95% by weight and better still from 70% to 90% by weight of the total weight of composition (B).

The compositions (A) and (B) according to the invention may also contain various adjuvants conventionally used in cosmetic compositions for dyeing keratin fibers in particular hair, such as, cationic, nonionic, amphoteric or zwitterionic surfactants different from betaine surfactants previously described, or mixtures thereof, cationic, nonionic, amphoteric or zwitterionic polymers, or blends thereof, mineral or organic thickeners, and in particular cationic, nonionic and amphoteric associative polymer thickeners, antioxidants, penetrating agents, sequestering agents, fragrances, buffers, dispersing agents, conditioning agents such as, for example, modified or unmodified, volatile or non-volatile silicones, such as amino silicones, film-forming agents, ceramides, preservatives, opacifiers or conductive polymers. Composition (B) may also comprise anionic surfactants, betaines and/or anionic polymers.

The above adjuvants are generally present in an amount for each of them of between 0.01% and 20% by weight relative to the weight of the compositions.

Compositions (A) and (B) are intended to be mixed together to obtain a dyeing composition which is applied to keratin fibers for dyeing keratin fibers.

The dyeing composition is presented for application to keratin fibers in the form of gel, or cream, preferably gel.

Preferably, the weight ratio between composition A and composition B in the dual-compartment device can range from 0.3 to 2, preferably from 0.5 to 1.5.

Method for Dyeing Keratin Fibres

Another object of the present invention relates to a method for dyeing keratin fibres, and in particular human keratin fibres, wherein the following steps are successively performed:

applying a sustained pressure to the closed envelop 2 in the region of at least one compartment 7a or 7b of the multiple-compartment device 1, in order to break the internal frangible seal 8, opening the closed envelop 2 of said multiple-compartment device, and applying the mixture of compositions (A) and (B), as previously defined, on said keratin fibres.

The mixture of compositions (A) and (B) is applied to wet or dry human keratin fibers.

Preferably, the sustained pressure is applied to the compartment 7b comprising the oxidation composition (B) in order to break the internal frangible seal 8.

After breaking the internal frangible seal 8, compositions (A) and (B) commingle instantly in order to provide a dyeing composition.

The dyeing composition may be mixed by shaking or turning upside-down the closed envelop 2.

The closed envelop 2 is then opened by way of tearing or cutting with a pair of scissors.

According to a preferred embodiment, the closed envelop 2 is opened by tearing the pre-cut line 14.

The dyeing composition thus obtained is then directly applied on the keratin fibres.

The composition is then left in place for a time usually ranging from 1 minute to 1 hour and preferably from 5 minutes to 30 minutes, more preferably from 5 minutes to 20 minutes, and better, from 5 to 10 minutes.

After the treatment, the human keratin fibers are optionally rinsed with water, optionally washed with a shampoo and then rinsed with water, before being dried or left to dry.

Examples

The following compositions A, A1, A2 and A3 were prepared, as shown in Table 1:

TABLE 1

| | % by weight of the active ingredients | | | |
| --- | --- | --- | --- | --- |
| Ingredients | A (invention) | A1 (comparative) | A2 (comparative) | A3 (comparative) |
| 2,4-Diaminophenoxyethanol HCl (24Dape Lo-Bleu from Dragon Chemical) | 0.8 | 0.8 | 0.8 | 0.8 |

TABLE 1-continued

| | % by weight of the active ingredients | | | |
|---|---|---|---|---|
| Ingredients | A (invention) | A1 (comparative) | A2 (comparative) | A3 (comparative) |
| Resorcinol (Resorcinol Technical Grade Flake from Indspec Chemical Corporation) | 1.6 | 2 | 2 | 2 |
| p-Phenylenediamine (PPDA 99.5% OR from Chemstar) | 2 | 2 | 2 | 2 |
| Carbomer (polyacrylic acid, Carbopol ® 980 Polymer from Lubrizol) | 0.6 | 0.7 | 0.7 | 0.7 |
| Acrylates/Beheneth-25 methacrylate copolymer (NOVETHIX L-10 POLYMER, from LUBRIZOL) | 0.3 | 0.3 | 0.3 | 0.3 |
| Sodium laureth sulfate containing 1 mol of ethylene oxide (70% SLES-L from Zhejiang Zanyu Technology) | 1.4 | 1.4 | 1.4 | 1.4 |
| Cocamidopropyl betaine (38% in solution, Tego betaine F50 from Evonik Gidschmidt) | 1.9 | — | — | — |
| Cocamidopropyl hydroxysultaine | — | — | 1.9 | — |
| Disodium cocoamphodiacetate | — | — | — | 1.9 |
| Ethanolamine (Amino-2-ethanol, Monoethanolamine Care from BASF) | 2.5 | 2.6 | 2.6 | 2.6 |
| EDTA | 0.1 | 0.1 | 0.1 | 0.1 |
| Ascorbic acid | 0.25 | 0.25 | 0.25 | 0.25 |
| Sodium meta bisulfite | 0.5 | 0.5 | 0.5 | 0.5 |
| Vegetable oils | 0.02 | 0.02 | 0.02 | 0.02 |
| fragrance | 0.5 | 0.5 | 0.5 | 0.5 |
| Water | Up to 100 | Up to 100 | Up to 100 | Up to 100 |

| ingredients | % by weight of the active ingredients Oxidizing composition B |
|---|---|
| Hydrogen peroxide | 7.5 |
| Polyquaternium-6 | 0.2 |
| Beheneth-10 | 0.06 |
| Cetearyl alcohol | 3.1 |
| Ceteareth-33 | 1.2 |
| Mineral oil | 0.56 |
| Tetrasodium etidronate | 0.06 |
| Tetrasodium pyrophosphate | 0.04 |
| preservative | qs |
| water | Up to 100 |

Compositions were introduced into a dual sachet made of a multilayer polyethylene film and divided into two iso-size compartments separated by a frangible seal.

A dual sachet according to the invention was obtained by introducing composition A in one compartment and composition B in the second compartment so that both compositions are not in contact during the time of storage. The weight ratio between composition A and composition B is equal to 1.

Comparative dual sachets were obtained by introducing respectively compositions A1, A2 and A3 in one compartment and composition B in the second compartment so that both compositions are not in contact during the time of storage. The weight ratio between composition A1, A2, A3 and composition B is equal to 1.

At the time of use, a hand-pressure was applied onto the dual sachet, enabling to break the seal in-between and allowing both compositions to easily mix together.

Locks of natural 90% grey hairs (NG) are treated with, respectively, dye composition mixture A+B (in an amount of 5 g of composition A+5 g of composition B), dye composition mixture A1+B (in an amount of 5 g of composition A1+5 g of composition B), dye composition mixture A2+B (in an amount of 5 g of composition A2+5 g of composition B), dye composition mixture A3+B (in an amount of 5 g of composition A3+5 g of composition B), which are then left on for 5 minutes at 27° C.

After this leave-on time, the locks are easily rinsed with water and then dried using blow dryer.

The compositions are easy to mix, easy to apply and to spread on the hair locks.

The colouring obtained is measured using a Minolta CM-2500d Spectrophotometer, especially the L* value which represents the colour intensity (Lightness value). The lower the value of L, the darker or more intense the colour.

| Results | L |
|---------|-------|
| A + B   | 20.02 |
| A1 + B  | 23.07 |
| A2 + B  | 23.6  |
| A3 + B  | 22.29 |

As can be seen in the table, the L value measured for the lock of hair treated with the dye composition A+B according to the present invention is lower than the L value measured for the locks of hair treated with the comparative dye compositions A1+B, A2+B and A3+B.

This shows that the color intensity of hair colored with the dye composition A+B according to the present invention is higher than the color intensity of hair coloured with the comparative compositions. These data demonstrate that the use of betaine amphoteric surfactant increases the intensity of hair coloring composition.

We claim:

1. A multiple-compartment device comprising:
    a closed envelope divided into at least two distinct compartments separated from one another by at least one internal frangible seal;
    at least two flexible sidewalls secured together along their peripheral edges, defining a sealed perimeter and an internal volume for the at least two distinct compartments;
    wherein the at least two distinct compartments comprise a first compartment and a second compartment;
    wherein the first compartment comprises a composition (A) comprising:
        a) at least one oxidation dye precursor;
        b) at least one anionic surfactant;
        c) at least one amphoteric surfactant chosen from betaine;
        d) optionally, at least one anionic associative polymer;
        e) optionally, at least one anionic non associative polymer; and
    wherein the second compartment comprises an oxidizing composition (B) comprising at least one oxidizing agent.

2. The device of claim 1, wherein the at least one oxidation dye precursor is selected from oxidation bases and couplers;
    wherein the oxidation bases are selected from para-phenylenediamines, bis(phenyl)alkylenediamines, para-aminophenols, ortho-aminophenols, heterocyclic bases, salts of organic or inorganic acid thereof, optical or geometric isomers thereof, tautomers thereof, solvates comprising hydrates thereof, or a mixture thereof; and
    wherein the couplers are selected from meta-aminophenols, meta-phenylenediamines and meta-diphenols, naphthols, mono- or polyhydroxylated naphthalene derivatives, and salts of organic or inorganic acid of heterocyclic coupler, optical or geometric isomers thereof, tautomers thereof, solvates comprising hydrates thereof, or a mixture thereof.

3. The device of claim 1, wherein the at least one oxidation dye precursor is selected from para-phenylenediamine, meta-aminophenol, meta-aminophenol, and meta-diphenol or resorcinol, salts of organic or inorganic acid of aminophenols, solvates comprising hydrates thereof, or a mixture thereof.

4. The device of claim 2, wherein at least one of the oxidation bases or the couplers is present in composition (A) in an amount ranging from 0.0001% to 10% by weight, relative to the total weight of the composition A.

5. The device of claim 1, wherein the at least one anionic surfactant is chosen from sulfate, sulfonate, carboxylic (or carboxylate) anionic surfactants, or a mixture thereof.

6. The device of claim 1, wherein the at least one anionic surfactant is present in composition (A) in an amount ranging from 0.1% to 10% by weight, relative to the total weight of the composition (A).

7. The device of claim 1, wherein composition (A) comprises at least one anionic associative polymer chosen from:
    (1) a first compound comprising at least one hydrophilic unit and at least one fatty-chain allyl ether unit, the hydrophilic unit comprising an ethylenic unsaturated anionic monomer,
    (2) a second compound comprising at least one hydrophilic unit of unsaturated olefinic carboxylic acid type and at least one hydrophobic unit of (C10-C30)alkyl ester of unsaturated carboxylic acid type,
    (3) maleic anhydride/C30-C38 α-olefin/alkyl maleate terpolymers,
    (4) acrylic terpolymers comprising:
        (a) approximately 20% to 70% by weight of a carboxylic acid having α,β-monoethylenic unsaturation,
        (b) approximately 20% to 80% by weight of a non-surfactant monomer having α,β-monoethylenic unsaturation other than (a),
        (c) approximately 0.5% to 60% by weight of a nonionic monourethane being a reaction product of a monohydric surfactant with a monoisocyanate having monoethylenic unsaturation, and
    (5) copolymers comprising, among monomers of the copolymers, a carboxylic acid having α,β-monoethylenic unsaturation and an ester of carboxylic acid having α,β-monoethylenic unsaturation and of an oxyalkylenated fatty alcohol.

8. The device of claim 1, wherein the at least one anionic associative polymer is chosen from copolymers comprising monomers comprising, a carboxylic acid having α,β-monoethylenic unsaturation and an ester of carboxylic acid having α,β-monoethylenic unsaturation and of an oxyalkylenated fatty alcohol which are obtained from copolymerization between 1) and 2):
    1) at least one ethylenically unsaturated mono or dicarboxylic acid monomer substituted by at least one, linear or branched, $(C_1-C_{10})$alkyl group; and
    2) at least one associative monomer which is an ester of formula (I):

$$A-O-(Alk-O)_z-(CH_2)_w-R^a \quad \quad (I)$$

wherein:
    A represents an ethylenically unsaturated acyclic residue, optionally containing an additional carboxylic group or a salt thereof, wherein the additional carboxylic group is esterified with a, linear or branched, $(C_1-C_{20})$alkyl group;
    $R^a$ represents an alkyl, a linear or branched, $(C_1-C_{30})$alkyl group, alkylaryl or arylalkyl group having from 1 to 30 carbon atoms wherein the alkyl group is linear or branched;

Alk represents a linear or branched $(C_1-C_6)$alkylene group comprising —$CH_2$—$CH(R^b)$—, wherein $R^b$ represents a hydrogen atom, or a $(C_1-C_4)$alkyl group comprising methyl or ethyl group;

z is an integer comprised inclusively between 0 and 100;

w is an integer comprised inclusively between 0 and 30;

wherein the formula (I) comprises at least one carboxyl group C(O)OH, or C(O)O-$Q^+$ wherein $Q^+$ represents cation chosen from an alkali metal, alkaline earth metal or ammonium.

9. The device of claim 1, wherein the at least one anionic associative polymer is selected from at least one of acrylates/beheneth-25 methacrylate copolymer, acrylates/steareth-20 methacrylate copolymer, acrylates/palmeth-25 acrylate copolymer, acrylates/steareth-20 itaconate copolymer, acrylates/ceteth-20 itaconate copolymer, acrylates/ceteth-20 methacrylate copolymer, acrylate/beheneth-25 itaconate copolymer, acrylate/palmeth-25 methacrylates copolymer, acrylate/steareth-50 acrylate copolymer, acrylates/palmeth-25 itaconate copolymer, or a mixture thereof.

10. The device of claim 1, wherein the at least one anionic associative polymer is present in an amount ranging from 0.01% to 5% by weight, based on the total weight of the composition (A).

11. The device of claim 1, wherein the composition (A) comprises the at least one anionic non associative polymer chosen from those obtained from at least one monomer of formula (II):

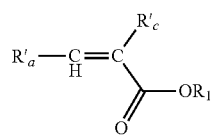

wherein:

$R'_a$ represents a hydrogen atom, or a linear or branched $(C_1-C_6)$alkyl group;

$R'_c$ represents a hydrogen atom, a linear or branched $(C_1-C_6)$alkyl group, a C(O)OX group, or a -alk-C(O)OX group, wherein X represents a hydrogen atom, an alkali metal, alkaline earth metal, or ammonium and -alk- represents a $(C_1-C_6)$alkylene group comprising methylene group;

and $R_1$ represents a hydrogen atom, an alkali metal, a alkaline metal, or a $(C_1-C_6)$alkyl group.

12. The device of claim 1, wherein the at least one anionic non associative polymer further comprises at least one cross-linking agent.

13. The device of claim 1, wherein the anionic non associative polymer is polyacrylic acid.

14. The device of claim 1, wherein the at least one anionic non associative polymer is present in composition (A) in an amount ranging from 0.01% to 2.5% by weight, based on the total weight of the composition (A).

15. The device of claim 1, wherein the composition (A) further comprises at least one alkaline agent.

16. The device of claim 1, wherein the composition (B) comprises an oxidizing agent chosen from hydrogen peroxide, persalts, urea peroxide, polythionates, alkali metal bromates, ferricyanides, peroxygenated salts, or a mixture thereof.

17. The device of claim 1, wherein the closed envelop comprises at least one sheet of polymeric film folded back thereon and sealed at peripheral edges thereof, wherein the sheet of polymeric film is a multilayer polymeric film comprising at least two layers of polymeric film.

18. The device of claim 1, further comprising an opening means configured with a pre-cut line parallel to a first end of the sealed perimeter.

19. A method for dyeing keratin fibers comprising:

applying a sustained pressure to a closed envelop in a region of at least one compartment of at least two distinct compartments of a multiple-compartment device, to break at least one internal frangible seal, wherein the at least two distinct compartments are separated from one another by the at least one internal frangible seal prior to being broken by the sustained pressure, and the at least two distinct compartments comprise a first compartment and a second compartment, opening the closed envelop, and applying a mixture of a composition (A) and a composition (B), on the keratin fibers, wherein the first compartment comprises the composition (A), and the second compartment comprises the composition (B) comprising at least one oxidizing agent, wherein the composition (A) comprises:

a) at least one oxidation dye precursor;

b) at least one anionic surfactant;

c) at least one amphoteric surfactant chosen from betaine;

d) optionally, at least one anionic associative polymer; and e) optionally, at least one anionic non associative polymer.

* * * * *